United States Patent
Hart

(10) Patent No.: US 7,815,646 B2
(45) Date of Patent: Oct. 19, 2010

(54) DRILL GUIDE AND METHOD FOR PLACING A FIXATION DEVICE HOLE

(75) Inventor: Rickey Hart, Marco Island, FL (US)

(73) Assignee: Karl Storz GmbH & Co. KG (DE)

( * ) Notice: Subject to any disclaimer, the term of this patent is extended or adjusted under 35 U.S.C. 154(b) by 399 days.

(21) Appl. No.: 11/759,036

(22) Filed: Jun. 6, 2007

(65) Prior Publication Data

US 2008/0306487 A1    Dec. 11, 2008

(51) Int. Cl.
A61B 17/58 (2006.01)
A61B 17/60 (2006.01)
A61F 2/00 (2006.01)

(52) U.S. Cl. ..................... 606/96
(58) Field of Classification Search ............... D24/140; 83/821–829; 401/99–117; 408/95, 97, 115 B, 408/115 R, 241 G, 79–81; 606/96–98; 623/22.12
See application file for complete search history.

(56) References Cited

U.S. PATENT DOCUMENTS

| | | | |
|---|---|---|---|
| 2,547,571 A * | 4/1951 | Ettinger | 606/96 |
| 4,669,473 A | 6/1987 | Richards et al. | |
| 4,672,957 A | 6/1987 | Hourahane | |
| 4,722,331 A | 2/1988 | Fox | |
| 4,733,654 A | 3/1988 | Marino | |
| 4,739,751 A | 4/1988 | Sapega et al. | |
| 4,781,182 A | 11/1988 | Purnell et al. | |
| 4,901,711 A | 2/1990 | Goble et al. | |
| 4,911,153 A | 3/1990 | Border | |
| 4,920,958 A | 5/1990 | Walt et al. | |
| 4,950,271 A | 8/1990 | Lewis et al. | |
| 5,026,376 A * | 6/1991 | Greenberg | 606/96 |
| 5,112,337 A | 5/1992 | Paulos et al. | |
| 5,154,720 A | 10/1992 | Trott et al. | |
| 5,163,940 A | 11/1992 | Bourque | |
| 5,234,434 A | 8/1993 | Goble et al. | |
| 5,300,077 A | 4/1994 | Howell | |
| 5,314,429 A | 5/1994 | Goble | |
| 5,320,626 A | 6/1994 | Schmieding | |
| 5,324,295 A | 6/1994 | Shapiro | |
| 5,330,468 A | 7/1994 | Burkhart | |
| 5,350,383 A | 9/1994 | Schmieding et al. | |
| 5,385,567 A * | 1/1995 | Goble | 606/96 |
| 5,454,816 A | 10/1995 | Ashby | |
| 5,458,602 A | 10/1995 | Goble et al. | |

(Continued)

OTHER PUBLICATIONS

European Search Report, EP08010257, Nov. 12, 2008, 5 pages.

*Primary Examiner*—Thomas C Barrett
*Assistant Examiner*—Larry E Waggle, Jr.
(74) *Attorney, Agent, or Firm*—St. Onge Steward Johnston & Reens LLC

(57) ABSTRACT

The invention relates to a drill guide and method for providing a drill guide, where the drill guide is for placing a fixation device hole proximate to a bone tunnel in a bone. The drill guide includes a foot for placement in the bone tunnel in the bone and a leg extending from the foot and having a recess. A locator is placed within the recess and, in a retracted position, the locator is inside the leg. The locator is also hingedly connected to the leg such that, in an unretracted position, the locator rotates and extends outwardly from the recess for locating a fixation device hole.

13 Claims, 9 Drawing Sheets

U.S. PATENT DOCUMENTS

| | | | |
|---|---|---|---|
| 5,514,144 A * | 5/1996 | Bolton | 606/96 |
| 5,562,664 A | 10/1996 | Durlacher et al. | |
| 5,584,839 A * | 12/1996 | Gieringer | 606/96 |
| 5,601,550 A * | 2/1997 | Esser | 606/54 |
| 5,601,566 A | 2/1997 | Dance et al. | |
| 5,613,971 A | 3/1997 | Lower et al. | |
| 5,643,273 A | 7/1997 | Clark | |
| 5,669,915 A * | 9/1997 | Caspar et al. | 606/96 |
| 5,681,320 A | 10/1997 | McGuire | |
| 5,683,400 A | 11/1997 | McGuire | |
| 5,688,284 A | 11/1997 | Chervitz et al. | |
| 5,891,150 A | 4/1999 | Chan | |
| 5,968,050 A | 10/1999 | Torrie | |
| 6,019,767 A | 2/2000 | Howell | |
| 6,120,511 A | 9/2000 | Chan | |
| 6,210,415 B1 | 4/2001 | Bester | |
| 6,254,604 B1 | 7/2001 | Howell | |
| 6,254,605 B1 | 7/2001 | Howell | |
| 6,342,057 B1 * | 1/2002 | Brace et al. | 606/96 |
| 6,547,795 B2 * | 4/2003 | Schneiderman | 606/96 |
| 7,144,424 B2 | 12/2006 | Steenlage | |
| 2004/0199170 A1 * | 10/2004 | Shluzas et al. | 606/105 |
| 2005/0137704 A1 * | 6/2005 | Steenlage | 623/13.14 |
| 2005/0177171 A1 * | 8/2005 | Wetzler et al. | 606/96 |

* cited by examiner

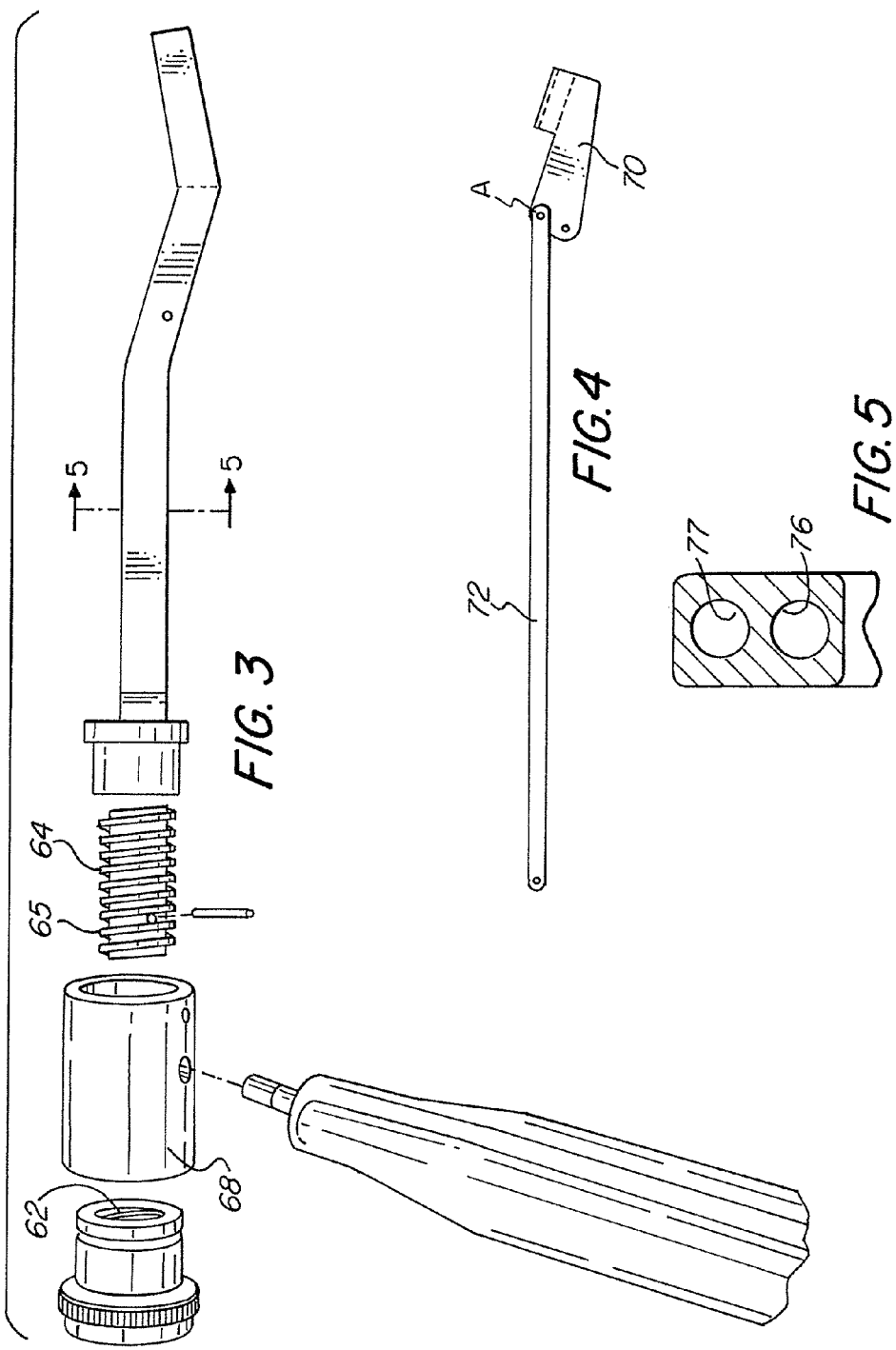

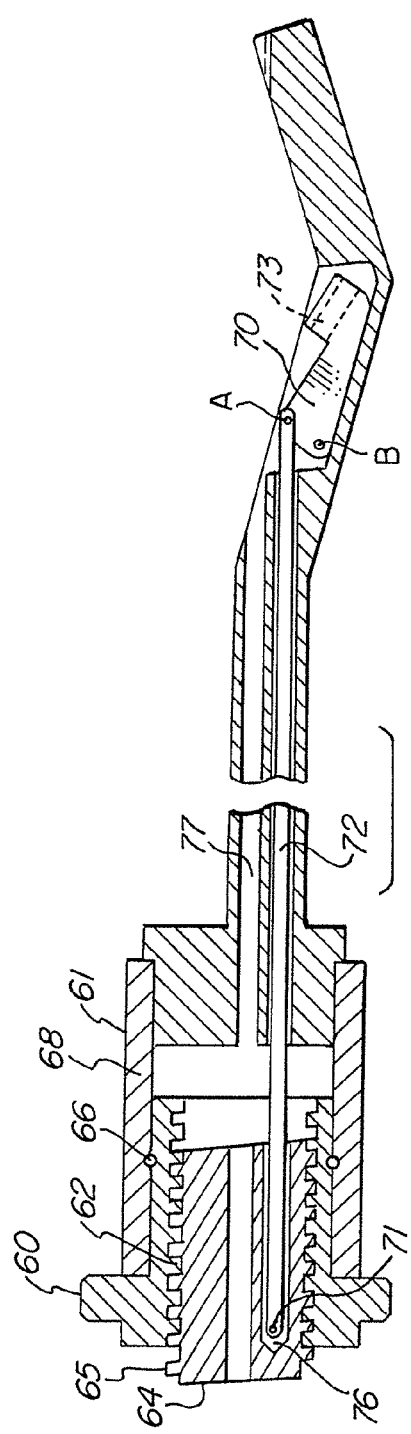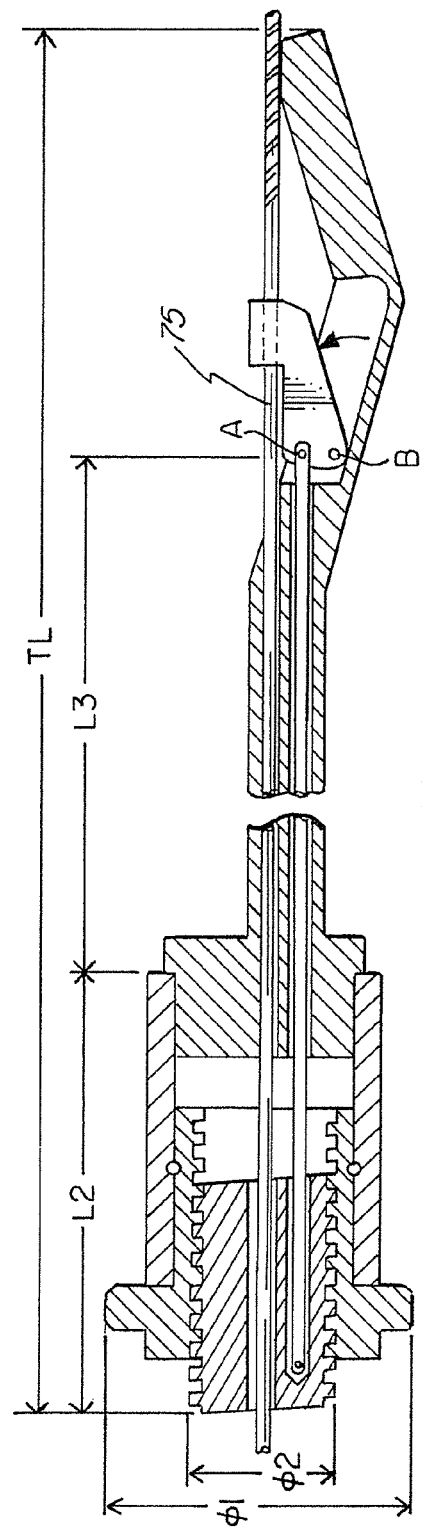
FIG. 6
FIG. 7

DRILL GUIDE AND METHOD FOR PLACING A FIXATION DEVICE HOLE

FIELD OF THE INVENTION

The invention relates to a drill guide and method of providing a drill guide.

BACKGROUND OF THE INVENTION

Stable healing of a tendon graft to an adjacent bone is often important in tendon or ligament reconstruction. Successful incorporation of the graft is typically dependent on two factors. First, the graft should be fixed in such a way as to maximize the contact area between the graft and the bone, thereby providing the greatest amount of surface area for graft incorporation. Second, the graft fixation should be stable, minimizing the amount of motion between graft and bone. This can minimize the amount of weak fibrous tissue that forms at the bone-graft interface and maximize the degree to which a more stable bone-soft tissue interface develops at the point of bone-graft contact.

More particularly, graft fixation techniques for bone to tendon graft healing often affects the successful incorporation of the graft. One graft fixation technique is the use of an interference screw, which typically improves the pullout strength of tendon grafts. In addition, better tunnel location, tunnel compaction, tighter graft/tunnel fit, improved graft preparation/suturing techniques, and the use of longer, biodegradable screws usually further contribute to increase the pullout strengths.

However, the interference screw itself on one side of the graft can limit the bone/graft contact to a portion of the graft'circumferential area. Some studies suggest stable bony ingrowth of the graft into the surrounding bone occurs at the outer rim of the bone tunnel. With the interference screw, this ingrowth may be limited to the side of the graft that is in direct contact with bone; the other half of the graft contacts the screw and hence is not available for bony ingrowth. Thus, it is possible that there is little or no bony ingrowth where the interference screw intervenes between the tendon graft and the host bone.

In addition, spinning of the tendon graft during insertion of the interference screw may be a problem that is difficult to control once it has begun. This "tendon spin" can damage the graft and result in impingement and less-than-ideal graft positioning, possibly affecting the clinical results.

Furthermore, the benefits of tunnel and graft preparation may be negated if poor technique is used in positioning the interference screw, in which case the screw may become loose or pulled out from the bone. Therefore, positioning of the screw, such as the distance from the bone tunnel and angle of placement, may greatly affect pullout values and can undo the benefits of a properly prepared bone tunnel and/or graft.

What is desired, therefore, is a tool and method for reducing tendon spinning. Another desire is a tool and method for increasing bony ingrowth. A further desire is a tool and method for properly positioning the interference screw and reducing the dependence on the user'technique.

SUMMARY OF THE INVENTION

It is therefore an object of the invention to provide a tool and method for reducing tendon spin when securing the tendon to the bone.

Another object is a tool and method for increasing bony ingrowth to promote better attachment of the tendon to the bone.

A further object is a tool and method for properly positioning the interference screw.

Yet another object is a tool and method for reducing the dependence of tendon attachment to the surgeon'technique.

These and other objects of the invention are achieved by a drill guide for placing a fixation device hole proximate to a bone tunnel in a bone, where the drill guide includes a foot for placement in the bone tunnel in the bone and a leg extending from the foot and having a recess. A locator is placed within the recess and, in a retracted position, the locator is inside the leg. The locator is also hingedly connected to the leg such that, in an unretracted position, the locator rotates and extends outwardly from the recess for locating a fixation device hole.

In some embodiments, the recess has a depth large enough so that, in the retracted position, the locator is placed entirely within the recess and the locator includes an orifice through which a guide wire is placed for drilling the fixation device hole. In other embodiments, the leg extends angularly from the foot so that the fixation device hole is drilled angularly as well as downwardly toward the bone tunnel.

In further embodiments, the drill guide has a knob for controlling the locator, which in turn varies a distance between a proposed fixation device hole and the bone tunnel. In some of these embodiments, a shaft is pivotably connected to the locator on one end of the shaft and connected to the knob at the other end of the shaft so that the shaft communicates movement of the knob to the locator.

In other embodiments, an adapter is connected to the shaft and the knob is threadedly engaged with the adapter, wherein rotation of the knob causes the adapter to translate, and therefore the shaft to also translate, in an axial direction. The translation of the shaft causes the locator to rotate about the pivotable connection between the locator and the leg. In this effort, a distance between a height of the locator in an unretracted position is based upon a rotation of the knob. Also, in an unretracted position, the locator extends toward the foot. In some embodiments, the foot includes a notch for receiving the guide wire.

In another embodiment, the drill guide includes a foot for placement in the bone tunnel in the bone, a leg extending from the foot and having a recess, and a locator placed within the recess such that, in a retracted position, the locator is inside the leg. The locator is also hingedly connected to the leg in a first location such that, in an unretracted position, the locator rotates and extends outwardly from the recess for locating the fixation device hole. At the same end as the connection to the leg, the locator is hingedly connected to a shaft in a second location, wherein movement of the shaft away from the foot transfers tensile forces to the locator via the second location and causes the locator to rotate about the first location to the unretracted position, and wherein movement of the shaft toward the foot transfers compressive forces to the locator and causes the locator to rotate about the first location to the retracted position.

In some embodiments, the drill guide has a knob in communication with the locator for controlling the locator to vary a distance between a proposed fixation device hole and the bone tunnel.

In another aspect of the invention, a method for providing the drill guide includes the steps of providing a foot for placement in the bone tunnel in the bone, extending a leg from the foot, placing a recess in the leg, and placing a locator within the recess of the leg for defining a retracted position. The method also hingedly connects the locator to the leg such that, in an unretracted position, the locator rotates and extends outwardly from the recess toward the proposed fixation device hole.

In some embodiments, the method angularly extends the leg from the foot. In other embodiments, the method controls the locator for varying a distance between the fixation device hole and the bone tunnel.

In further embodiments, the method pivotably connects the locator with a shaft for controlling the shaft, which in turn varies a distance between the fixation device hole and the bone tunnel. In some of these embodiments, a threaded knob is connected to the shaft for controlling the locator. In further embodiments, the method determines a number of revolutions of the knob based on the distance between the fixation device hole and the bone tunnel.

In another embodiment, the method pivotably connects the locator to the leg such that translation of the shaft In an axial direction causes the locator to rotate about the pivotable connection with the leg.

BRIEF DESCRIPTION OF THE DRAWINGS

FIG. 3 depicts an assembly view of the drill guide shown in FIG. 1

FIG. 4 more particularly depicts the locator shown in the drill guide of FIG. 1.

FIG. 5 depicts a cross sectional view of the drill guide shown in FIG. 3.

FIG. 6 depicts a cross sectional view of the drill guide shown in FIG. 1.

FIG. 7 depicts another cross sectional view of the drill guide shown in FIG. 1.

FIG. 12 depicts the guide wire for insertion into the drill guide shown in FIG. 1.

DETAILED DESCRIPTION OF THE INVENTION

Figure 1:
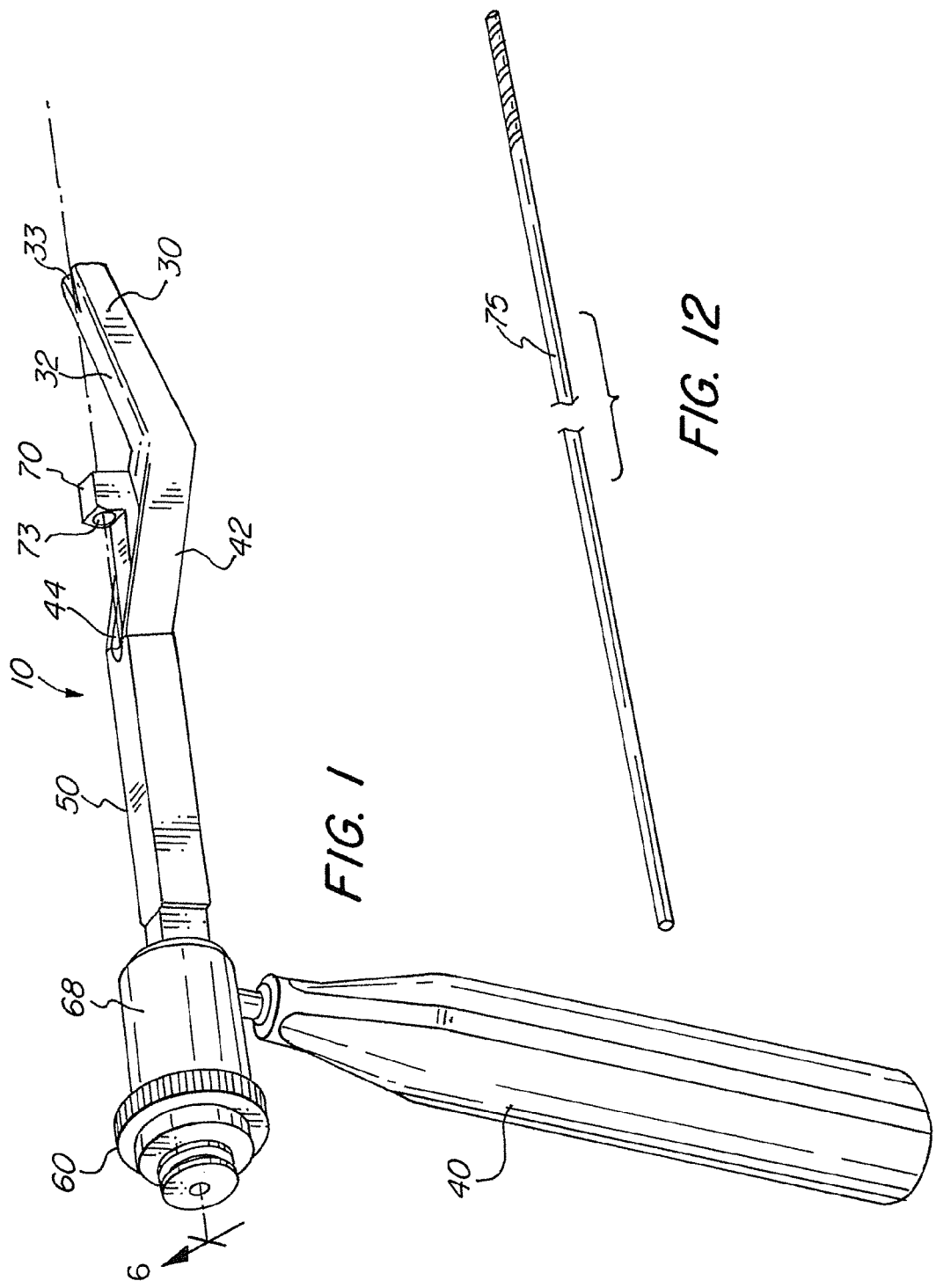
FIG. 1 depicts the drill guide in accordance with the invention.

As shown in FIG. 1, drill guide 10 includes foot 30, handle 40 for maneuvering drill guide 10, and leg 50 between foot 30 and handle 40. As shown, leg 50 includes sloped section 42 that is angled downwardly toward foot 30. The sloped section being angled relative to the foot increases the likelihood of the fixation device hole being drilled downwardly toward the bone tunnel.

Figure 2:
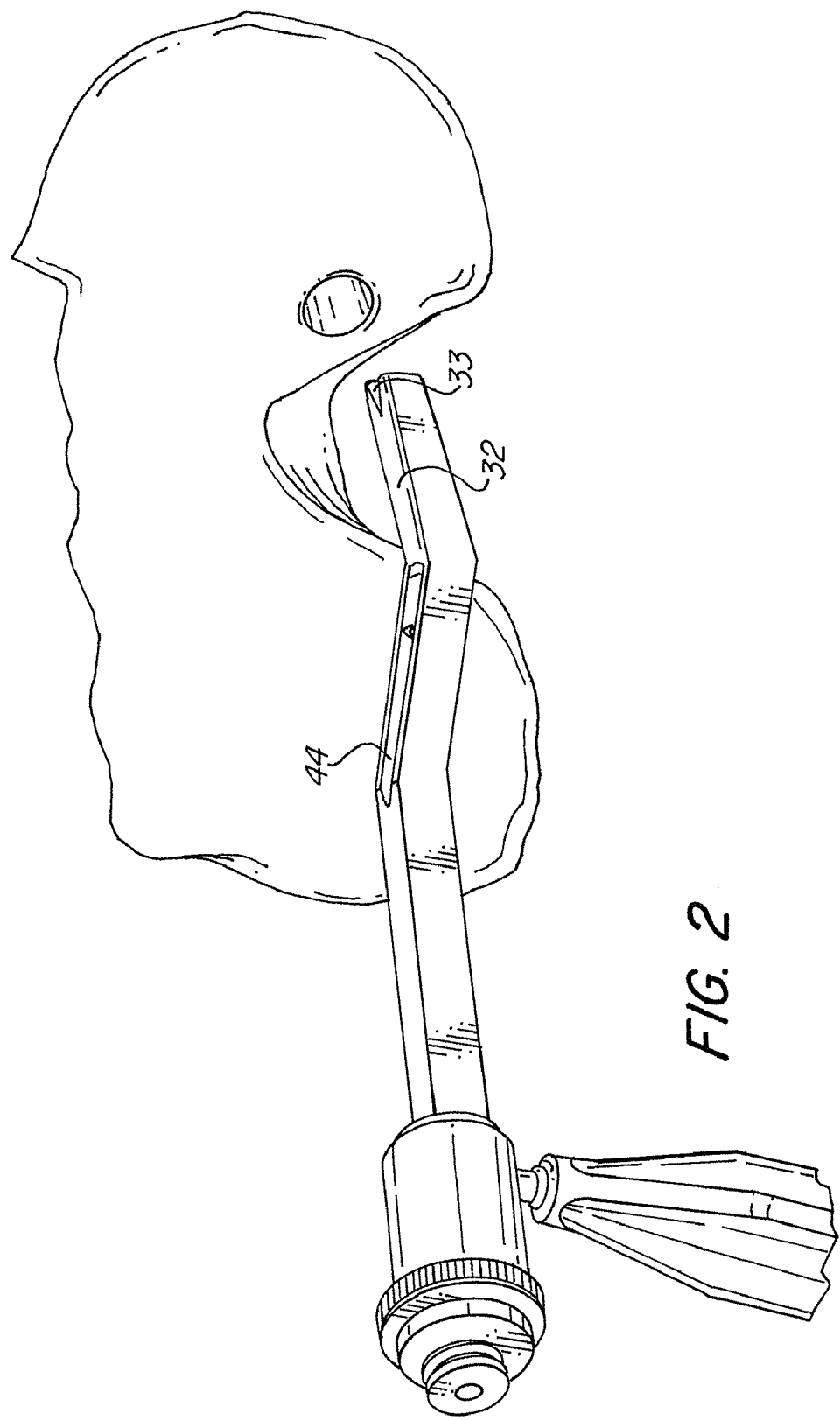
FIG. 2 depicts the drill guide shown in FIG. 1 being inserted into a bone tunnel.

As shown more particularly in FIGS. 2-3, drill guide 10 also has knob 60 for controlling locator 70 to move locator in and out of recess 44. When locator 70 is placed within recess 44, leg 50 and foot 30 are more easily inserted into a body member than if locator 70 was separate from or outside of leg 50, where the body member includes skin, tissue, muscle, and the like, all of which would be cut so that locator 70 would reach bone 22. With locator 70 within recess 44 and within sloped section 42, drill guide 10 is more easily maneuvered since there is in essence is single item, namely leg 50, to maneuver than a drill guide with two items, namely the leg and locator 70 being separable from one another or at least where one is not placed inside the other. Another benefit of placing locator 70 within recess 44 is that a single cut, and also a smaller cut, is made into the body member.

As shown, threads 62 are engaged with adapter 64 and adapter 64 is connected to shaft 72 such that rotation of knob 60 causes a translation of adapter 64 and a translation of adapter 64 in turn causes axial movement of shaft 72.

As shown in FIG. 6, threads 62 of knob 60 is threadedly engaged or mated with threads 65 of adapter 64. However, there is no or negligible rotational movement between knob 60 and adapter 64 due to shaft 72 inhibiting such movement, where shaft 72 extends through leg 50 and adapter 64 via lower channel 76. Because there is inhibited rotational movement yet threaded engagement between knob 60 and adapter 64, adapter 64 thus moves axially when knob 60 is rotated.

When adapter 64 moves axially relative to knob 60, shaft 72 also moves axially relative to knob 60 because shaft 72 is affixed or pinned to adapter 64 via pin 71. In other embodiments, pin 71 is replaced with rivet, fastener, or the like.

Knob 60 is held in place via cross pin 66, which secures knob 60 and housing 68 together and inhibits axial movement between knob 60 and housing 68 but permits rotational movement between knob 60 and housing 68. In some embodiments, cross pin 66 is replaced by any structure that secures housing 68 to knob 60 but permits rotational movement of knob 60 relative to housing 68, such as bearings, a snap ring, or a bushing.

As shown, lower channel 76 is a bored hole through adapter 64 and through hole through sloped section 42, where the bored hole and through hole align with one another. In some embodiments, lower channel 76 is not the bored hole shown in adapter 64 but instead extends all the way through, or is a through hole, which is similar to upper channel 77. All that is required of lower channel 76 is that is has a length long enough to accommodate shaft 72. As shown, upper channel 77 is a through hole penetrating each of adapter 64 and leg 50, where the through holes align with one another.

The operation of drill guide 10 is for the purpose of raising locator 70 from recess 44 to a fully extended position where guide wire 75 (see FIG. 12) is, after passing through hole 73, in a position to drill fixation device hole 24 (see FIG. 11) in bone 22.

Figure 9:
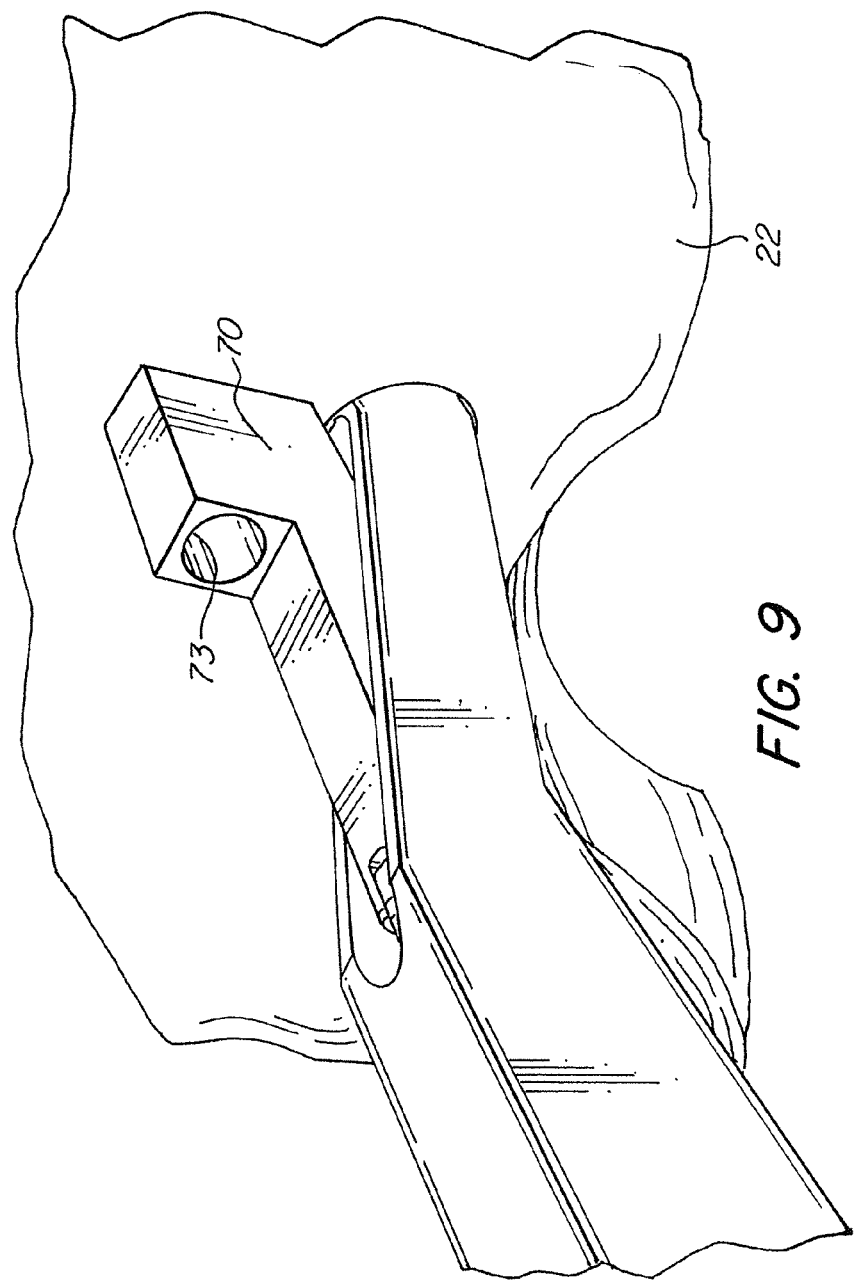
FIG. 9 depicts the drill guide of FIG. 1 inserted into the bone tunnel, where the locator is in an unretracted position.
Figure 10:
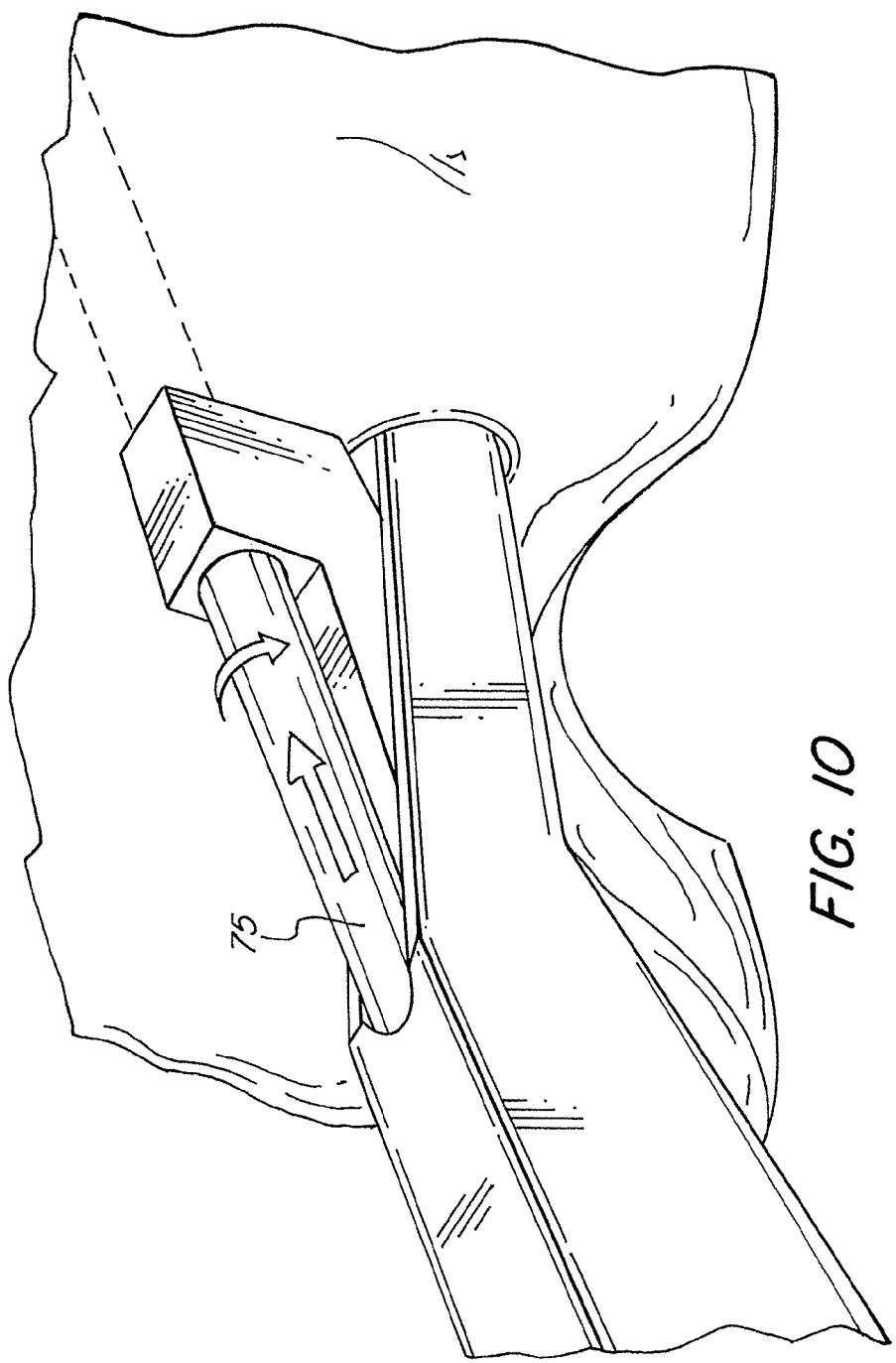
FIG. 10 depicts the drill guide of FIG. 1 inserted into the bone tunnel, where the locator is in an unretracted position and guide wire is passed through the locator.

As shown in FIG. 2, bone tunnel 21 is drilled into bone 22 through any known or novel manner. Foot 30 is placed within bone tunnel 21 (FIG. 8) until leg 50 comes in contact with bone 22. Once in this position, the user rotates knob 60 in order to raise locator 70 outwardly from recess 44 to the unretracted position shown in FIG. 9 (locator 70 more particularly described below). As discussed above, guide wire 75 is then passed through hole 73 in locator 70 to commence drilling of fixation device hole 24 (FIG. 10).

As stated above, the user rotates knob 60 so that adapter 64 and therefore shaft 72 move axially, where the axial movement of shaft 72 causes locator 70 to rotate about location B, where such rotation results in locator 70 extending outwardly from recess 44 toward the fully unretracted position.

As shown in FIGS. 4, 6, and 7, locator 70 is hingedly connected to shaft 72 at location A, where a pin, rivet, and the like are placed at location A to secure locator 70 and shaft 72 together, and where locator and shaft 72 freely rotate relative to one another. Also as shown, locator 70 is hingedly attached at location B to sloped section 42, where location B includes the same limitations as location A. In this fashion, axial translation of shaft 72 causes locator 70 to rotate or pivot about location B, where the translation or tensile/pull force of shaft 72 are transferred at hinged location A to locator 70. As locator 70 rotates about location B, locator 70 is raised upwards and outwards from recess 44 (see the direction of rotation represented by the arrow shown in FIG. 7).

Figure 8:
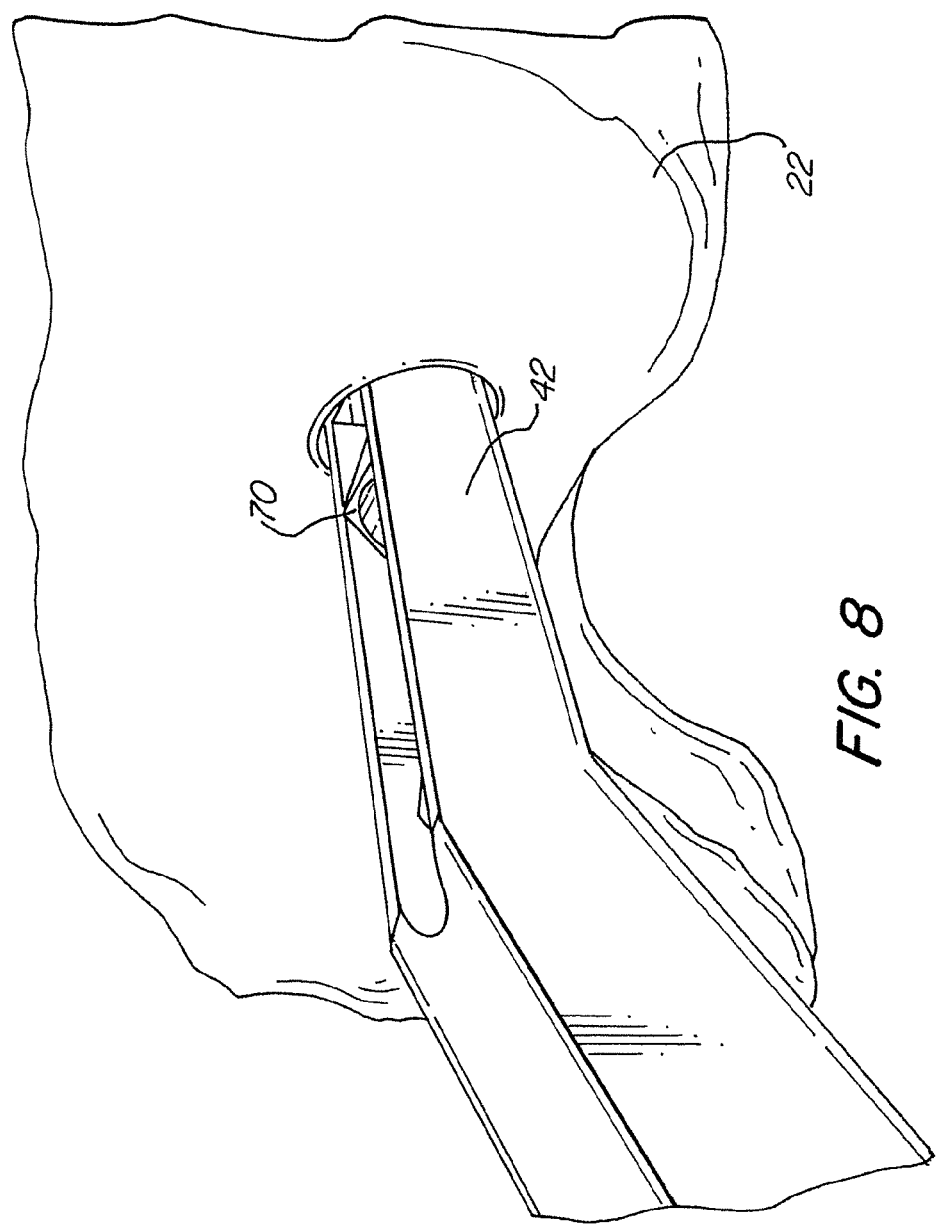
FIG. 8 depicts the drill guide of FIG. 1 inserted into the bone tunnel, where the locator is in a retracted position.

As shown in FIG. 8, in the fully retracted position, locator 70 is completely within an interior of sloped section 42. As shown in FIG. 9, in a fully unretracted position, locator 70 extends outwardly from recess 44. To rotate locator 70 from the unretracted position to the retracted position, knob 60 is rotated the opposite direction from the immediate paragraph, which causes shaft 72 to translate in an opposite direction, resulting in a compressive/push force being transferred at hinged location A to locator 70. The compressive force causes locator 70 to rotate about location B.

Figure 11:
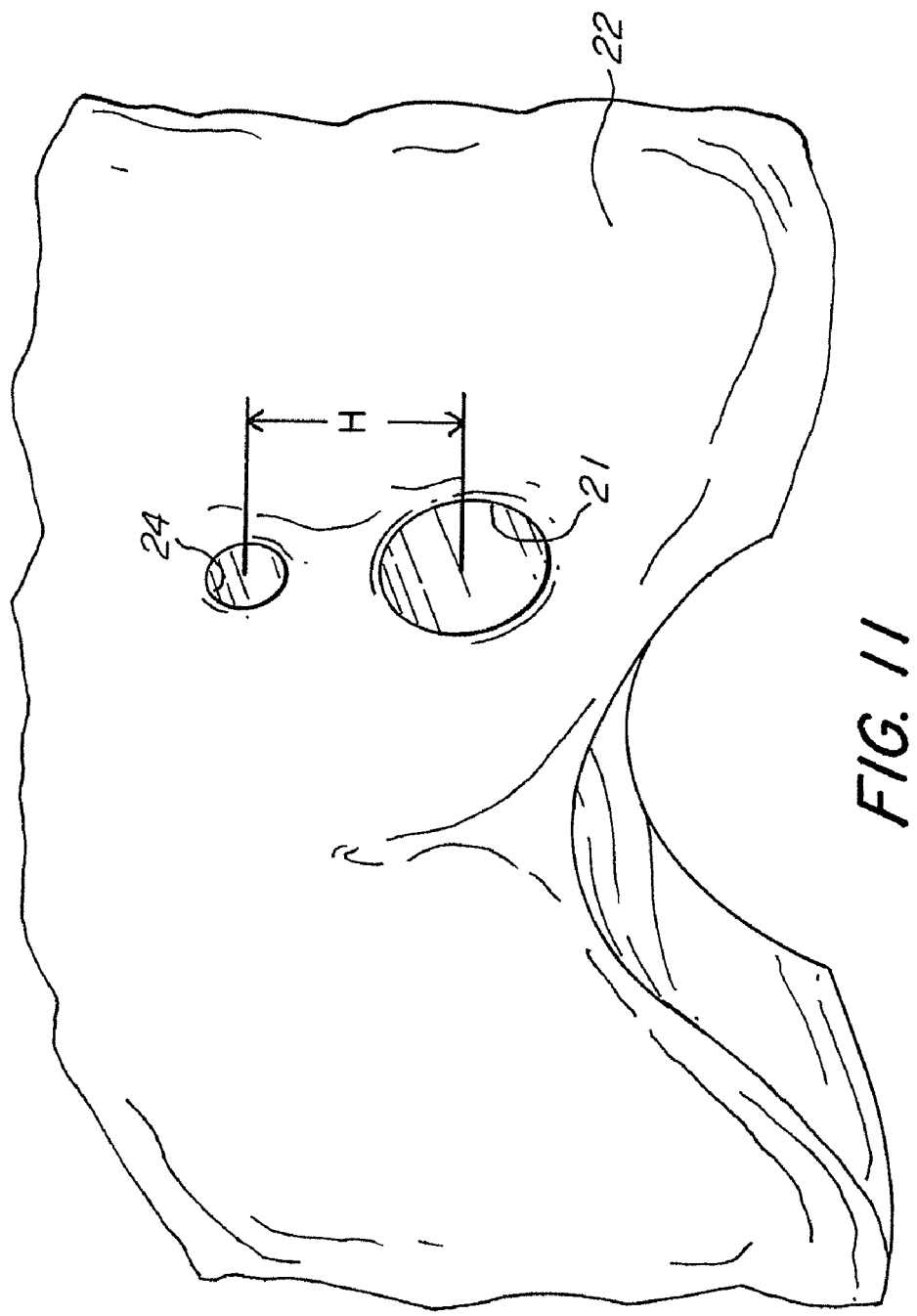
FIG. 11 depicts the fixation device hole provided by the drill guide shown in FIG. 1.

The distance between fixation device hole 24 and bone tunnel 21, represented in FIG. 11 by H, is typically between approximately 3 mm and approximately 6 mm, and preferably between approximately 4 mm and approximately 5 mm. In some embodiments, distance H is important because it usually dictates the size of the bone wedge, which is in general terms the wedge of bone between fixation device hole 24 and bone tunnel 21. A small H may lead to a thin and easily cracked bone wedge when subjected to pressure from fixation device. A large H may lead to difficulty in cutting bone wedge. Therefore, maintaining a proper distance between fixation device hole 24 and bone tunnel 21 is desired to be within the above mentioned ranges.

To this end, a relationship between a number of rotations of knob 60 and height H of locator 70 is known. The relationship involves threads 62 of knob 60, length of shaft 72, placement of hinged connection A, placement of hinged connection B, and angle of sloped section 42. During the manufacture of drill guide 10, all of these factors in the relationship will be known. Therefore, the distance H will be known for any given rotation of knob 60.

More specifically, in some embodiments, a ratio of rotation of knob 60 to rotation of locator 70 is 18:1. Therefore, for every 18 degrees of rotation of knob 60, locator 70 is rotated 1 degree about location A in an outwardly direction from recess 44.

In some of the above embodiments, the total length (indicated as TL in FIG. 7) of drill guide 10 from end to end is approximately 6.5 inches, the length of knob 60 and outer bushing 61 (indicated as L2) is approximately 1.5 inches, the length of drill guide 10 from the end of outer bushing 61 to location A (indicated as L3) is approximately 3.394 inches, the outermost diameter of knob 60 is approximately 1 inch (indicated as Ø 1), the diameter of adapter 64 is approximately 0.5 inch (indicated as Ø 2), and the pitch of adapter and knob threads 62 and 65 is approximately 10 threads per inch.

In further embodiments, a full rotation of knob 60 means shaft 72 translates approximately 0.100 inches. As shown, the total axial movement of shaft is approximately 0.075 inches, which means knob 60 rotates approximately 270 degrees.

In other embodiments, a lateral distance between locations A and B is approximately 0.133 inches, which means for every approximate 0.0023 inch of axial movement of shaft 72, locator 70 is rotated approximately 1 degree. In a preferred embodiment, locator 70 rotates a total of approximately 27 degrees between fully extended and fully retracted positions. Multiplying 0.0023×27 degrees=0.062 inches, which represents the approximate axial movement of locator 70.

The difference between 0.075 and 0.062 inches (0.013 inches) represents the standard of deviation (or slop or measurement error) in a lateral direction due to the stack up from knob 60 to location B. This is a reason for the approximate 27 degree rotation of locator 70 when approximately 15 degrees is all that is needed, where 15 degrees is the approximate angular relation of sloped section 42 relative to foot 30. The approximate 27 degree rotation is to compensate for the approximate 0.013 inch slop, where the over-rotation of locator 70 ensures that the fully retracted and fully extended positions are met. Under ideal circumstances, there would not be any 0.013 inch measurement error in the lateral direction and, therefore, movement in a lateral direction would be the approximate 0.062 inch axial travel of locator 70 and locator would not need to rotate beyond 15 degrees.

In further embodiments, to reduce knob rotation, the ratio is reduced to 15:1 or 12:1. In yet other embodiments, the ratio is 10:1. In embodiments where fine tuning is preferred, whereby locator 70 is rotated in fractions of degrees and H is measured in tenths of inches or millimeters, the ratio is increased to between 20:1 to 30:1, such as 25:1

Another way to reduce knob rotation would be to reduce pitch of threads 62, 65 to, for example, 8 threads per inch. The result would be a reduced knob rotation of approximately ½ turn or approximately 180 degrees. Conversely, increasing pitch would achieve the fine tuning stated above In some embodiments, the distance H is fixed where locator 70 is in a fully retracted position or a fully unretracted position, where there would not be any positions in between. There would be a mechanical stop on knob 60 letting the user know when to stop rotating knob 60, where rotation reaching this point means locator 70 has extended fully from recess 44.

In other embodiments, the user of drill guide 10 wishes to vary the distance H to a position between the fully retracted and fully unretracted positions. Because the relationship between revolutions of knob 60 and locator 70, the distance H is known. Hence, a user desiring a particular distance H would know how many revolutions are needed and rotate knob 60 to those revolutions. Vice versa, a person rotating knob 60 would know after so many turns the distance H, the desired distance between the fully retracted and unretracted positions, is achieved and then stop rotating knob 60.

In some embodiments, while turning knob 60, the distance H is always known due to a read out of H on a display. Therefore, the user will know when to stop rotating knob 60. In some of these embodiments, the read out or display simply measures the rotations of knob 60 and calculates the relative distance of locator 70 to bone tunnel 21, typically on centers.

The fineness of threads 62 or how close the threads are to one another affects the axial translation of shaft 72. The finer the threads, the more slowly the axial translation and, hence, more revolutions of knob 60 are needed to translate shaft 72 than a coarsely threaded knob. Additionally, the finer the threads, the more accurate or exact H may be set by the user, particularly if H is measured to the tenths of an inch, hundredths of an inch, and the like.

Once the desired H is achieved and locator 70 is in the unretracted position (as stated above in the alternative embodiment, this does not necessarily mean the fully unretracted position), guide wire 75 is inserted into upper channel 77 through adapter 64, is passed through leg 50, and through hole 73 of locator 70 toward bone 22. See FIG. 10. After contacting bone 22, guide wire 75 is rotated to drill into bone 22, thereby providing fixation device hole 24 through bone 22.

As shown, fixation device hole may be a blind hole, meaning the user cannot visually determine or has reduced visual contact with the end of guide wire 75, and therefore has difficulty determining when fixation device hole 24 is complete or when bone 22 has been penetrated completely through.

In some embodiments, guide wire 75 continues penetrating bone 22 until guide wire 75 comes in contact with foot 30, and more particularly channel 32 and notch 33 of foot 30. Channel 32 receives guide wire 75 and reduces the likelihood of guide wire 75 being skewed or missing foot 30 in a lateral direction. In addition, channel 32 directs guide wire 75 toward notch 33, where in some embodiments a sensor is placed at notch 33 for sensing contact with guide wire 75. Once the sensor senses guide wire 75, a signal is sent to a receiver proximate to the user for indicating to the user that guide wire 75 is in contact with notch 33 and/or channel 32 and therefore has penetrated through bone 22. In yet other embodiments, the sensor is sensitive to metal, which is the material of guide wire 75. In some of these embodiments, the sensor visually detects guide wire 75 making contact with bone 22. In other embodiments, the invention envisions other means for informing the user that guide wire 75 has passed through bone and that fixation device hole 24 is complete.

Figure 13:
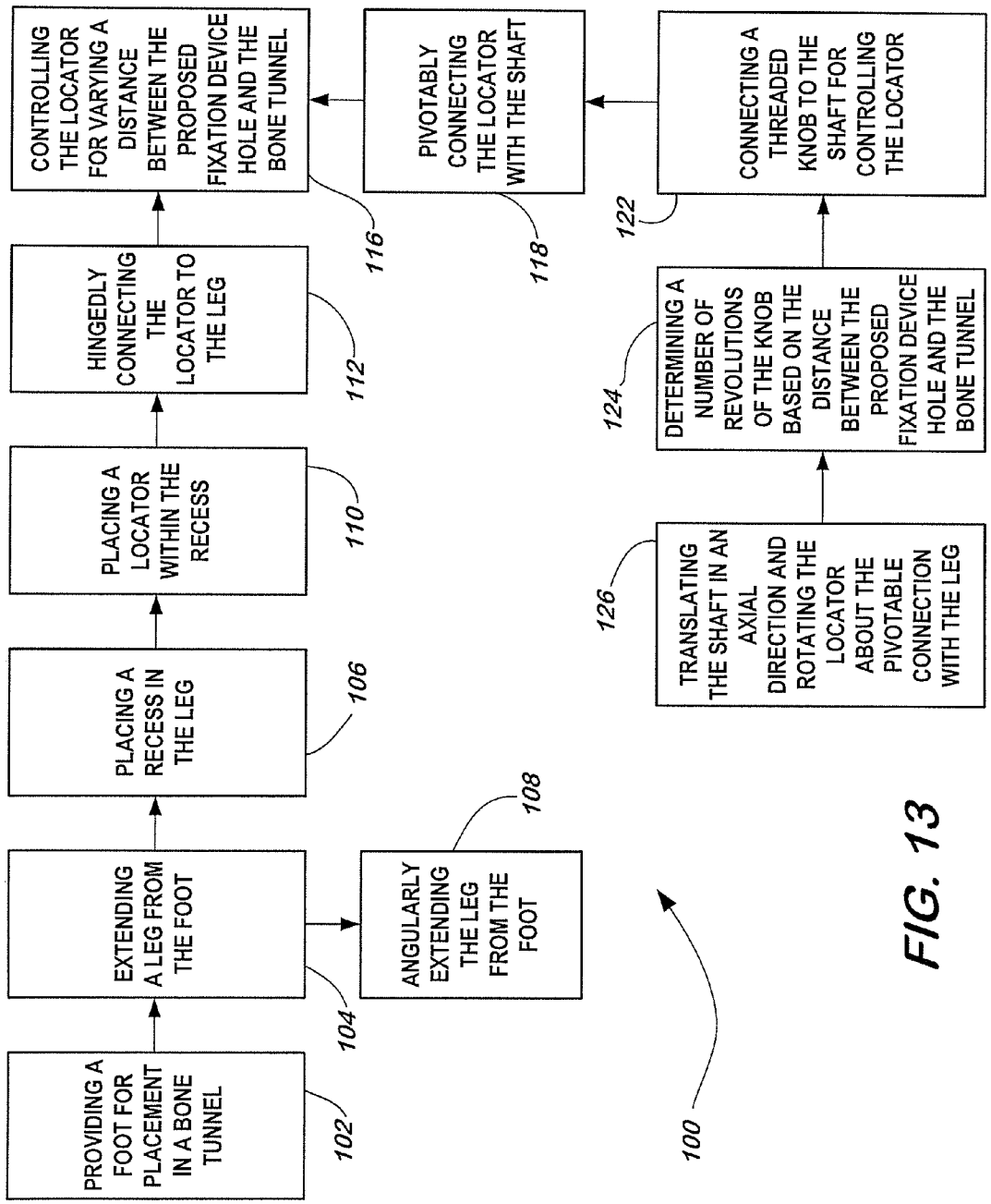
FIG. 13 depicts a method of providing the drill guide shown in FIG. 1.

In another aspect of the invention, FIG. 13 depicts method 100 for providing the drill guide shown in FIG. 1 for placing a proposed fixation device hole proximate to bone tunnel 21 in bone 22, including the steps of providing 102 a foot for placement in the bone tunnel, extending 104 a leg from the foot, placing 106 a recess in the leg, and placing 110 a locator within the recess, which is the retracted position. In some of these aspects, the leg is angularly extended 108 from the foot to better position the fixation device hole at an angle toward the bone tunnel.

Method 100 also includes hingedly connecting 112 the locator to the leg for permitting the locator to pivot in and out of the recess from the retracted to the unretracted positions, the unretracted position being where the locator rotates and extends outwardly from the recess.

Method 100 also has the step of controlling 116 the locator for varying a distance between the proposed fixation device hole and the bone tunnel. In some embodiments, this step includes pivotably connecting 118 the locator with a shaft that is placed within the leg, connecting 122 a threaded knob to the shaft on the opposite side as the locator, where rotation of the knob causes the locator to pivot out of and/or into the recess.

In further embodiments, controlling the locator also includes determining 124 a number of revolutions of the knob based upon the distance between the proposed fixation device hole and the bone tunnel. In other embodiments, this includes translating 126 the shaft in an axial direction and rotating the locator about the hinged, or pivotable, connection with the leg.

What is claimed is:

1. A drill guide for placing a fixation device hole proximate to a bone tunnel in a bone, comprising:
   a foot for placement in the bone tunnel in the bone;
   a leg extending from said foot and having a recess;
   a locator placed within said recess and, in a retracted position, said locator is entirely inside said leg; and
   said locator hingedly connected to said leg such that, in an unretracted position, said locator rotates and extends outwardly from said recess for locating the fixation device hole.

2. The drill guide according to claim 1, wherein said locator includes an orifice through which a guide wire is placed for drilling the fixation device hole.

3. The drill guide according to claim 1, wherein said leg extends angularly from said foot.

4. The drill guide according to claim 1, further comprising a knob in communication with said locator for controlling said locator to vary a distance between a proposed fixation device hole and the bone tunnel.

5. The drill guide according to claim 1, wherein said recess has a depth large enough so that, in the retracted position, said locator is placed entirely within said recess.

6. The drill guide according to claim 4, further comprising a shaft between said locator and said knob for communicating movement of said knob to said locator, wherein said shaft is pivotably connected to said locator.

7. The drill guide according to claim 6, further comprising an adapter threadedly engaged with said knob, and said adapter is connected to said shaft such that rotation of said knob causes said adapter to move in an axial direction and this causes said shaft to translate in an axial direction.

8. The drill guide according to claim 7, wherein translation of said shaft causes said locator to rotate about said pivotable connection between said locator and said leg.

9. The drill guide according to claim 4, wherein a height of said locator is based upon a rotation of said knob.

10. The drill guide according to claim 1, wherein, in an unretracted position, said locator extends toward said foot.

11. The drill guide according to claim 2, wherein said foot includes a notch for receiving the guide wire.

12. A drill guide for placing a fixation device hole proximate to a bone tunnel in a bone, comprising:
   a foot for placement in the bone tunnel in the bone;
   a leg extending from said foot and having a recess;
   a locator placed within said recess and, in a retracted position, said locator is inside said leg;
   said locator hingedly connected to said leg in a first location such that, in an unretracted position, said locator rotates and extends outwardly from said recess for locating the fixation device hole;
   said locator is hingedly connected to a shaft in a second location;
   wherein movement of said shaft away from said foot transfers tensile forces to said locator via said second location and causes said locator to rotate about said first location to the unretracted position; and
   wherein movement of said shaft toward said foot transfers compressive forces to said locator and causes said locator to rotate about said first location to the retracted position.

13. The drill guide according to claim 12, further comprising a knob in communication with said locator for controlling said locator to vary a distance between a proposed fixation device hole and the bone tunnel.

* * * * *